United States Patent [19]

Willis et al.

[11] 4,272,412
[45] Jun. 9, 1981

[54] HALOGEN CONTAINING IONONE DERIVATIVES AND COMPOSITIONS CONTAINING SAME

[75] Inventors: Brian J. Willis, Bergenfield; Philip A. Christenson, Midland Park, both of N.J.; Robert Mack, Valley Stream, N.Y.

[73] Assignee: Fritzsche Dodge & Olcott Inc., New York, N.Y.

[21] Appl. No.: 129,898

[22] Filed: Mar. 13, 1980

[51] Int. Cl.³ .................. C07C 49/11; C07C 49/21; A61K 7/46
[52] U.S. Cl. .................. 252/522 R; 568/376; 568/377; 568/378
[58] Field of Search .............. 252/522; 568/376, 377, 568/378

[56] References Cited

U.S. PATENT DOCUMENTS 3,852,355  12/1974  Rautenstrauch et al. .......... 568/376

OTHER PUBLICATIONS

Gavin et al., "Helv. Chim Acta", vol. 61, (1978), pp. 352–357.
Arctander, "Per. & Flavor Chem" (1969) Compounds No. 370, 608 & 2272.
House, "Modern Syn. Reactions", 2nd Ed., pp. 434–435, (1972).
Mookherjee et al., *Isolation and Identification of Volitile Constituents of Tincture of Ambergris*, Paper No. 136, VII International Congress of Essential Oils, Kyoto, Japan (1977).

*Primary Examiner*—Norman Morgenstern
*Attorney, Agent, or Firm*—Cooper, Dunham, Clark, Griffin & Moran

[57] ABSTRACT

The present invention relates to novel compounds useful as fragrance materials which have the structure

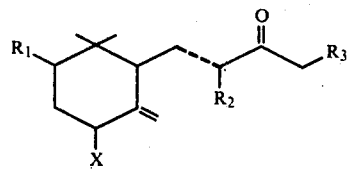

wherein the dashed line may be either a carbon-carbon single bond or a carbon-carbon double bond; $R_1$, $R_2$ and $R_3$ are each the same or different and each represents hydrogen or methyl; and X is halogen. The invention also provides methods of preparing these compounds from readily available cyclohexene derivatives and fragrance compositions which include the compounds.

6 Claims, No Drawings

HALOGEN CONTAINING IONONE DERIVATIVES AND COMPOSITIONS CONTAINING SAME

BACKGROUND OF THE INVENTION

There is an increased demand for materials which can be used to modify and/or enhance the organoleptic properties of consumable items. The natural oils which have traditionally been used for this purpose often suffer the disadvantages of irregular or limited supply, variable quality and high cost. Consequently the search for new and inexpensive chemicals which can be used as partial or total replacements for essential oils, or which can be used in the creation of new and unique flavor and fragrance materials has intensified in recent years.

The use of halogen containing compounds as fragrance materials is well documented. One example is gamma homocyclogeranyl chloride which has the general structure

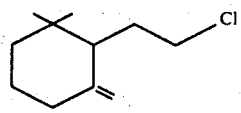

and is a component of tincture of Ambergris. 2-Chloro-3-methoxy-5-methylphenol and 2,4-dimethoxy-6-methyl chlorobenzene have been found in *Evernia Prunastri*. Further examples may be found in Actander, *Perfume and Flavor Chemicals* (1969). For example alphabromostyrol which has the structure

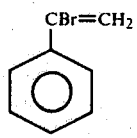

is identified as compound No. 370 in Actander. Its fragrance is described therein as pungent-sweet, grassy-floral odor, reminiscent of Hyacinth in extreme dilution. Slightly softer than the odor of omega-Bromostyrol.

Actander compound No. 608 is 2-chloro-4,6-dinitro-1,3-dimethyl-5-tertiary-butylbenzene which has the structure

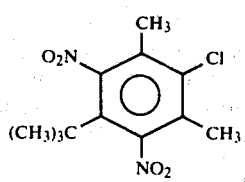

and is described as having an odor similar to 2,4,6-trinitro-3-tertiary-butyl toluene, sweet, heavy, musky, slightly more pungent and less tenacious.

Actander compound No. 2272 is mononitro dibromobutylmeta-cresol methylether which has the structure

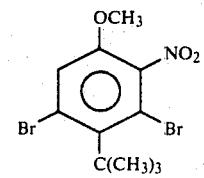

and is described as having a sweet Ambergris musk-like odor of good tenacity.

SUMMARY OF THE INVENTION

In accordance with the present invention it has been found that compounds having the structure

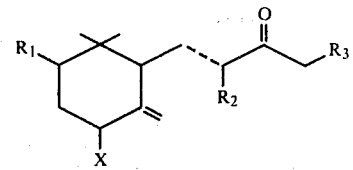

wherein the dashed line may be either a carbon-carbon single bond or a carbon-carbon double bond; $R_1$, $R_2$ and $R_3$ are each the same or different and each represents hydrogen or methyl, and X represents a halogen group are useful as fragrance materials.

The present invention also provides efficient and economical processes for preparing these compounds involving reacting a substituted cyclohexene derivative having the structure

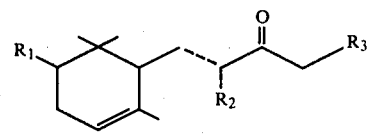

wherein the dashed line may be either a carbon-carbon single bond or a carbon carbon double bond and $R_1$, $R_2$ and $R_3$ are each the same or different and each represents hydrogen or methyl with a hypohalous acid having the formula HO-X wherein X is halogen.

Finally in accordance with the present invention it has been found that fragrance compositions can be prepared by incorporating in these compositions the novel compounds of this invention.

DETAILED DESCRIPTION OF THE INVENTION

In accordance with this invention, there have been discovered novel halogen-containing cyclohexane derivatives as represented by the structure

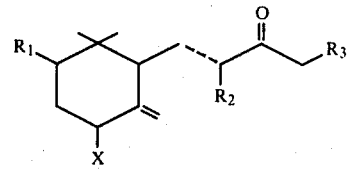

wherein the dashed line may either be a carbon-carbon single bond or a carbon-carbon double bond; $R_1$, $R_2$ and $R_3$ are each the same or different and each represents hydrogen or methyl; and X represents a halogen group have been prepared. It will be recognized that the chemicals of this invention can exist in several stereoisomeric forms. The foregoing structural formula is intended to embrace the individual stereoisomers, as well as mixtures of the various stereoisomers of the halogen compounds of this invention. The compounds exhibit clean, soft, powdery, warm, sweet, woody orris, berry-like notes rendering them useful in fine fragrances as well as perfumed products such as deodorants, cosmetic preparations and the like.

The compounds of this invention can be conveniently and inexpensively prepared by reacting a cyclohexene derivative having the structure

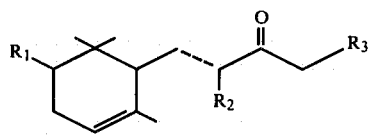

wherein the dashed line may be either a carbon-carbon single bond or a carbon-carbon double bond and $R_1$, $R_2$ and $R_3$ are each the same or different and each represents hydrogen or methyl with a hypohalous acid having the general formula HO-X, where X is selected from a group consisting of the halogens chlorine, bromine or iodine, preferably chlorine or bromine in the presence of an organic solvent such as methylene dichloride, ethylene dichloride, hexane or toluene, preferably methylene dichloride or ethylene dichloride. The hypohalous acid is generated in situ in accordance with standard procedures (see H. O. House, "Modern Synthetic Reactions," 2nd ed., p. 434 (1972). Isolation and purification of the final products is achieved by conventional techniques including extraction, distillation, preparative chromatographic techniques and the like.

One or more of the halogen-containing cyclohexane derivatives of this invention and auxiliary perfume ingredients, for example, alcohols, aldehydes, ketones, nitriles, esters and essential oils may be admixed so that the combined odors of the individual components produce a desired fragrance. Such perfume compositions are carefully balanced, harmonious blends of essential oils, aroma chemicals, resinoids and other extracts of natural odorous materials. Each ingredient imparts its own characteristic effect to the composition. Thus, one or more of the halogen-containing compounds of this invention can be employed to impart novel characteristics into fragrance compositions.

Such compositions may contain up to about 80 weight percent of any one or more of the halogen containing cyclohexane derivatives of the invention. Ordinarily at least 0.001 weight percent of the halogen-containing cyclohexane derivative is required to impart significant odor characteristics. Amounts in the range of from about 1 to about 60 weight percent are preferred. The halogen-containing compounds of this invention may be formulated into concentrates containing about 1 to 60 weight percent of the chemical in an appropriate solvent. Such concentrates are then employed to formulate products such as colognes, deodorants, etc., wherein the concentration of the chemicals of this invention can be in the range of from about 0.001 to about 7 weight percent depending upon the final product.

A number of examples are provided hereinafter to illustrate the preferred embodiments of this invention, but are in no way meant to limit the scope thereof.

The following instrumentation was used to characterize the novel compounds of this invention. Nuclear Magnetic Resonance (NMR) spectra were recorded with a Varian Associates T-60A spectrometer using tetramethylsilane as the internal reference. Infrared (IR) spectra were obtained with a Perkin Elmer 710 B spectrophotometer. Mass spectra (MS) were obtained with a Hewlett-Packard 5985 Mass Spectrometer. Unless otherwise stated weights are in grams, temperatures are in degrees centigrade and pressures in mm Hg.

EXAMPLE 1

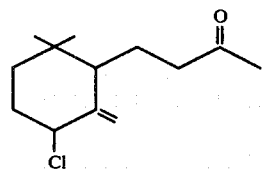

To a mixture of commercial bleach (28.5 ml of a 5.25% solution of sodium hypochlorite) α-dihydro-ionone (3.88 g) and methylene chloride (110 ml) was added a solution of potassium phosphate (monobasic) (5.44 g) in water (40 ml) during a 15 minute period. The mixture was stirred for 1 hour at 25°. The methylene chloride solution was washed with sodium bicarbonate solution, the solvent evaporated, and the residue distilled to give 2.81 g (61% yield) of 4-(5-chloro-6-methylene-2,2-dimethylcyclohexyl)-2-butanone, bp 101°-106°, 0.2 mm. NMR (CDCl$_3$) δ0.85 and 0.95 (6H,2s,>C(CH$_3$)$_2$), 0.9-2.6 (9H, m), 2.10 (3H, s, —COCH$_3$), 4.36-4.55 (1H, t, J=6 Hz,>CHCl), 4.76 and 5.33 (2H,2s,>C=(CH$_2$)). IR (film) γmax 2950, 1720, 1675, 1650, 1455, 1360. MS m/e 193, 175, 159, 134, 119.

EXAMPLE 2

The reaction of α-dihydro-ionone and hypochlorous acid was carried out as described in Example 1 except that hexane was substituted for methylene chloride. A 59% yield of 4-(5-chloro-6-methylene-2,2-dimethylcyclohexyl-2-butanone was obtained. The spectral data was identical to that reported in Example 1.

EXAMPLE 3

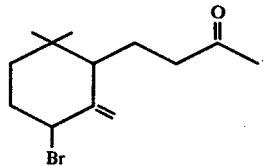

A solution of sodium bromide (6.17 g) in water (10 ml) and commercial bleach (31.2 ml of a solution of sodium hypochlorite) were stirred together for 5 minutes and a solution of dihydro-α-ionone (3.88 g) in methylene chloride was added. Then a solution of potassium phosphate (monobasic) (5.44 g) in water (30 ml) was added during 30 minutes. After stirring for 50 minutes at 25° a solution of sodium bromide (2.05 g) and commercial bleach (10 ml) was added, followed by a solution of potassium phosphate (monobasic) (2.72 g) in water (10 ml) and the reaction mixture stirred for 15 minutes at 25°. The methylene chloride solution was washed with sodium bicarbonate solution and the solvent evaporated to provide the crude product (5.86 g). Column chromatography gave 1.87 g of 4-(5-bromo-6-methylene-2,2-dimethylcyclohexyl)-2-butanone. NMR (CDCl$_3$) δ0.93 (6H, s, >C(CH$_3$)$_2$), 0.9–2.6 (9H, m), 2.12 (3H, s, —COCH$_3$), 4.6–5.1 (1H, m, >CHBr), 4.76 and 5.28 (2H, 2s, >C=CH$_2$), 4.68 and 5.20 (2H, 2s, >C=CH$_2$, minor isomer; isomer ratio 3/1). IR (film) ν$_{max}$ 2960, 1720, 1675, 1650, 1455, 1360.

EXAMPLE 4

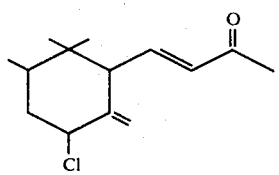

To a mixture of commercial bleach (42.6 ml of a 5.25% solution of sodium hypochlorite), α-irone (6.24 g), and methylene chloride (200 ml) was added a solution of potassium phosphate (monobasic) (8.16 g) in water (40 ml) during a 30 minute period. The mixture was stirred for 1 hour at 25°. The methylene chloride solution was washed with sodium bicarbonate solution and evaporated to give 7.3 g of crude product. Purification by column chromatography gave 4.59 g of 4-(5-chloro-6-methylene-2,2,3-trimethylcyclohexyl)-3-buten-2-one. NMR (CDCl$_3$) δ0.70–0.78 (2H, d, J=5 Hz, >CHCH$_3$), 0.90, 0.93 and 0.99 (6H, 3s, >C(CH$_3$)$_2$), 0.9–1.3 (1H, m, >CHCH$_3$), 1.5–2.1 (2H, m, —CH$_2$—), 2.25, 2.26 and 2.28 (3H, 3s, —COCH$_3$), 2.67 and 2.83 (1H, 2s, >CH—CH=CH—), 4.6–4.9 (1H, m, >CHCl), 4.93 and 5.12 (2H, 2s, >C=CH$_2$, 5.8–6.3 (1H, m, —CH=CH—CO—), 6.6–7.6 (1H, m, —CH=CH-CO—). IR (film) ν$_{max}$ 2960, 1695, 1675, 1620, 1460, 1430 cm$^{-1}$. MS m/e 207, 163.

EXAMPLE 5

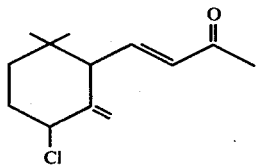

To a mixture of commercial bleach (28.5 ml of a 5.25% solution of sodium hypochlorite), α-ionone (3.84 g), and methylene chloride (330 ml) was added a solution of potassium phosphate (monobasic) (5.44 g) in water (40 ml) during a 30 minute period. The mixture was stirred for 30 minutes at 25°, the methylene chloride solution washed with sodium bicarbonate solution and evaporated to give 4.1 g of crude product. Purification by column chromatography gave 2.35 g of 4-(5-chloro-6-methylene-2,2-dimethylcyclohexyl)-3-buten-2-one. NMR (CDCl$_3$) δ0.90 and 0.93 (6H, 2s, >C(CH$_3$)$_2$), 0.9–2.1 (4H, m), 2.27 (3H, s, —COCH$_3$), 2.53 and 2.71 (1H, 2s, >CH—CH=CH—), 4.35–4.68 (1H, m, >CHCl), 4.70, 4.83, 5.15 and 5.33 (2H, 4s, >C=CH$_2$), 5.9–6.4 (1H, m, —CH=CH—CO—), 6.7–7.3 (1H, —CH=CH—COCH$_3$). IR (film) ν$_{max}$ 2960, 1695, 1675, 1630, 1450, 1430 cm$^{-1}$. MS m/e 191, 149.

EXAMPLE 6

The following illustrates the utility of 4-(5-chloro-6-methylene-2,2-dimethyl-1-cyclohexyl)-2-butanone, the compound of Example 1, in a fantasy floral composition.

| pts/wt | FANTASY FLORAL Component |
|---|---|
| 10 | Oil Patchouly |
| 10 | Eugenol Extra |
| 10 | Geranyl Acetate |
| 10 | Anisyl Acetate |
| 20 | Iso Eugenol |
| 20 | Hexyl Cinnamic Aldehyde |
| 20 | Hydroxy Citronellal |
| 20 | Oil Ylang Extra |
| 25 | 1% Sol. Aldehyde C-12 MNA in D.E.P. Odorless |
| 30 | Geraniol |
| 30 | Vetiveryl Acetate |
| 40 | Phenyl Ethyl Alcohol |
| 50 | Coumarin |
| 50 | Musk Ketone |
| 50 | Oil Bergamot |
| 60 | Oil Lemon |
| 70 | Vanillin |
| 75 | Compound of Example 1 |
| 100 | Heliotropin Extra |
| 100 | Benzyl Acetate |
| 100 | Linalool |
| 100 | Linalyl Acetate |
| 1000 | |

EXAMPLE 7

The following illustrates the utility of 4-(5-bromo-6-methylene-2,2-dimethyl-1-cyclohexyl)-2-butanone, the compound of Example 3, in fragrance compositions of the fougere type.

| pts/wt | FOUGERE Component |
|---|---|
| 20 | Oil Vetiver Reunion |
| 20 | 10% Sol. Rose Oxide in D.E.P. Colorless |
| 20 | Labdanum Resinoid Absolute |
| 30 | Coumarin |
| 30 | 10% Sol. Aldehyde C-11 in D.E.P. Odorless |
| 30 | Oil Patchouly |
| 30 | Oil Geranium Maroc |
| 30 | Citronellal Extra |
| 30 | Geraniol |
| 30 | Iso Amyl Salicylate |
| 30 | Eugenol |
| 40 | Linalool FCC |
| 50 | Oil Lemon |
| 50 | Oil Fir Needles Canadian |
| 50 | Linalyl Acetate |
| 50 | Phenyl Ethyl Alcohol |
| 50 | Hexyl Cinnamic Aldehyde |
| 100 | Oil Lavandin Abrial Extra |
| 100 | Cedryl Acetate |
| 100 | Compound of Example 3 |
| 110 | Diethyl Phthalate |
| 1000 | |

EXAMPLE 8

A fantasy woody floral fragrance may be prepared containing the compound of Example 4.

| pts/wt | FANTASY WOODY FLORAL Component |
|---|---|
| 60 | Rhodinol Extra |
| 10 | Phenylethyl Phenylacetate |

-continued

FANTASY WOODY FLORAL

| pts/wt | Component |
|---|---|
| 100 | Phenyl Ethyl Alcohol |
| 50 | Oil Rose Bulgarian |
| 30 | Oil Ylang Extra |
| 40 | Jasmin Absolute |
| 60 | Linalool |
| 50 | Benzyl Acetate |
| 140 | Oil Vetiver Reunion |
| 50 | Acetyl Cedrene |
| 30 | 10% Aldehyde C-11 in D.E.P. Odorless |
| 70 | Musk Ketone |
| 40 | Coumarin |
| 30 | Amyl Cinnamic Aldehyde |
| 130 | Hydroxycitronellal |
| 110 | Compound of Example 4 |
| 1000 | |

What is claimed is:

1. A compound defined by the generic structure

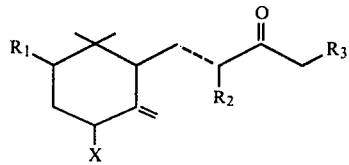

wherein the dashed line may be either a carbon-carbon single bond or a carbon-carbon double bond; $R_1$, $R_2$ and $R_3$ are each the same or different and each represents hydrogen or methyl; and X is halogen.

2. A compound in accordance with claim 1 wherein the dashed line represents a carbon-carbon single bond, $R_1$, $R_2$, and $R_3$ are hydrogen, and X is bromine.

3. A compound in accordance with claim 1 wherein the dashed line represents a carbon-carbon single bond, $R_1$, $R_2$ and $R_3$ are hydrogen, and X is chlorine.

4. A fragrance composition which comprises an amount of the compound of claim 1 effective to impart fragrance thereto in combination with conventional fragrance ingredients.

5. A fragrance composition which comprises an amount of the compound of claim 2 effective to impart fragrance thereto in combination with conventional fragrance ingredients.

6. A fragrance composition which comprises an amount of the compound of claim 3 effective to impart fragrance thereto in combination with conventional fragrance ingredients.

* * * * *